United States Patent
Fuerst et al.

(10) Patent No.: US 11,007,027 B2
(45) Date of Patent: May 18, 2021

(54) SURGICAL ROBOTIC USER INPUT APPARATUS HAVING OPTICAL FIBER-BASED INTRINSIC SENSORS

(71) Applicant: Verb Surgical Inc., Mountain View, CA (US)

(72) Inventors: Bernhard A. Fuerst, Sunnyvale, CA (US); Berk Gonenc, Cupertino, CA (US); Dennis Moses, Hollywood, FL (US); Pablo E. Garcia Kilroy, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 155 days.

(21) Appl. No.: 16/286,873

(22) Filed: Feb. 27, 2019

(65) Prior Publication Data
US 2019/0274768 A1 Sep. 12, 2019

Related U.S. Application Data

(60) Provisional application No. 62/639,969, filed on Mar. 7, 2018.

(51) Int. Cl.
*A61B 34/00* (2016.01)
*G01L 1/24* (2006.01)
*G01D 5/353* (2006.01)
*G06F 3/0346* (2013.01)
(Continued)

(52) U.S. Cl.
CPC .............. *A61B 34/70* (2016.02); *A61B 34/37* (2016.02); *A61B 34/74* (2016.02);
(Continued)

(58) Field of Classification Search
CPC ......... A61B 34/70; A61B 34/74; A61B 34/37; A61B 2034/2061; A61B 2034/742;
(Continued)

(56) References Cited

U.S. PATENT DOCUMENTS

| | | | | |
|---|---|---|---|---|
| 5,923,318 A | * | 7/1999 | Zhai ..................... | G06F 3/0346 345/156 |
| 2004/0037485 A1 | * | 2/2004 | Kersey ................ | G02B 6/0218 385/12 |

(Continued)

OTHER PUBLICATIONS

E. Fujiwara, D. Y. Miyatake, M. F. M. dos Santos and C. K. Suzuki, "Development of a glove-based optical fiber sensor for applications in human-robot interaction," 2013 8th ACM/IEEE International Conference on Human-Robot Interaction (HRI), Tokyo, 2013, pp. 123-124, doi: 10.1109/HRI.2013.6483532. (Year: 2013).*

(Continued)

*Primary Examiner* — Nathan J Jenness
(74) *Attorney, Agent, or Firm* — Womble Bond Dickinson (US) LLP

(57) ABSTRACT

A surgical robotic user input apparatus has a fiber optic cable with a handheld user input device attached at one end, and a connector attached at another end. Multiple intrinsic sensors, such as fiber Bragg grating sensors, are in the fiber optic cable. The intrinsic sensors are used to detect a pose of the handheld user input device. Other embodiments are also described and claimed.

20 Claims, 6 Drawing Sheets

(51) Int. Cl.
*A61B 34/37* (2016.01)
*G02B 6/02* (2006.01)
*A61B 34/20* (2016.01)
*A61B 90/00* (2016.01)

(52) U.S. Cl.
CPC .......... *G01D 5/35316* (2013.01); *G01L 1/246* (2013.01); *A61B 2034/2061* (2016.02); *A61B 2034/742* (2016.02); *A61B 2090/064* (2016.02); *G02B 6/02076* (2013.01); *G06F 3/0346* (2013.01)

(58) Field of Classification Search
CPC ... A61B 2090/064; G01L 1/246; G01L 5/226; G01D 5/35316; G01D 5/35377; G02B 6/02076; G02B 6/022
See application file for complete search history.

(56) References Cited

U.S. PATENT DOCUMENTS

2007/0156019 A1* 7/2007 Larkin ................... B25J 19/025
 600/104
2009/0137952 A1* 5/2009 Ramamurthy ....... A61B 5/4887
 604/95.01
2011/0202069 A1* 8/2011 Prisco ................... A61B 34/30
 606/130
2011/0302694 A1* 12/2011 Wang .................... A61B 5/103
 2/160
2014/0326078 A1* 11/2014 Arkwright ......... G01K 11/3206
 73/862.624

OTHER PUBLICATIONS

Bridge Health Monitoring with Fiber Optic Sensors; White Paper; Cleveland Electric Laboratories; Nov. 6, 2008; (www.clevelandelectriclabs.com> pp. 1-35.

Pixel-based Optical Fiber Tactile Force Sensor for Robot Manipulation, by Hui Xie, Allen Jiang, Lakmal Seneviratne, Kaspar Althoefer Sensors, 2012 IEEE, Taipei, Taiwan, 2012, pp. 1-4.

Optical Fibre Pressure Sensors in Medical Applications, by S Poeggel D Tosi, DB Duraibabu, G Leen, D McGrath and Elfed Lewis; (Sensors 2015) <www.mdpi.com/journal/sensors> pp. 17115-17148.

* cited by examiner

SURGICAL ROBOTIC USER INPUT APPARATUS HAVING OPTICAL FIBER-BASED INTRINSIC SENSORS

This nonprovisional patent application claims the benefit of the earlier filing date of provisional application No. 62/639,969 filed Mar. 7, 2018.

An embodiment of the invention relates to user input devices for the control of surgical robotic arms and tools. Other embodiments are also described.

BACKGROUND

In surgical robotic systems for teleoperation purposes, user input device tracking provides accurate sensing of user intent and control a stable and robust motion of a surgical robotic arm and an attached surgical robotic tool. Mechanisms for spatial tracking of a user input device known as electromagnetic trackers have been used, but do not fulfill the precision (e.g., noise problem) and latency requirements of surgical robotic systems. If the resulting information is not free of noise, drift and immune to magnetic interference from the environment, the error of the pose estimate of the user input device may generate undesired movement of the arm or tool, especially when sub-mm (for position or translation) and sub-degree (for orientation) precision may be needed. To reduce noise, the signal from the user input devices can be filtered, though at the expense of introducing latency, which also is not desirable.

SUMMARY

A surgical robotic user input apparatus and related method, in various embodiments, are described. Various embodiments include a fiber-optic cable with intrinsic sensors that is attached to a user input device.

In one embodiment, a surgical robotic user input apparatus has a handheld user input device (handheld UID) that is attached to a fiber-optic cable. The fiber-optic cable has intrinsic sensors. The fiber-optic cable has a first end with a connector that may be pluggable with (e.g., into) a connector of a stationary site such as a user console, and a second end. The hand-held user input device is attached to the second end of the fiber-optic cable. The intrinsic sensors are used to detect a pose of the handheld UID. The pose includes a three-dimensional position of the handheld UID and a rotation or orientation of the handheld UID, e.g., relative to the stationary first end.

One embodiment of the invention is a method of operating a surgical robotic user input apparatus, for tracking a user input device. The method includes sending first light into a fiber-optic cable that has intrinsic sensors, and receiving second light from the fiber optic cable. The first light may be modified by the intrinsic sensors. A pose of a hand-held user input device, that is attached to a second end of the fiber-optic cable, is determined by processing the sensed or received second light. The pose is a three-dimensional position and a rotation or orientation. The determined pose is continually updated, resulting in the tracking of the user input device.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

Figure 1:
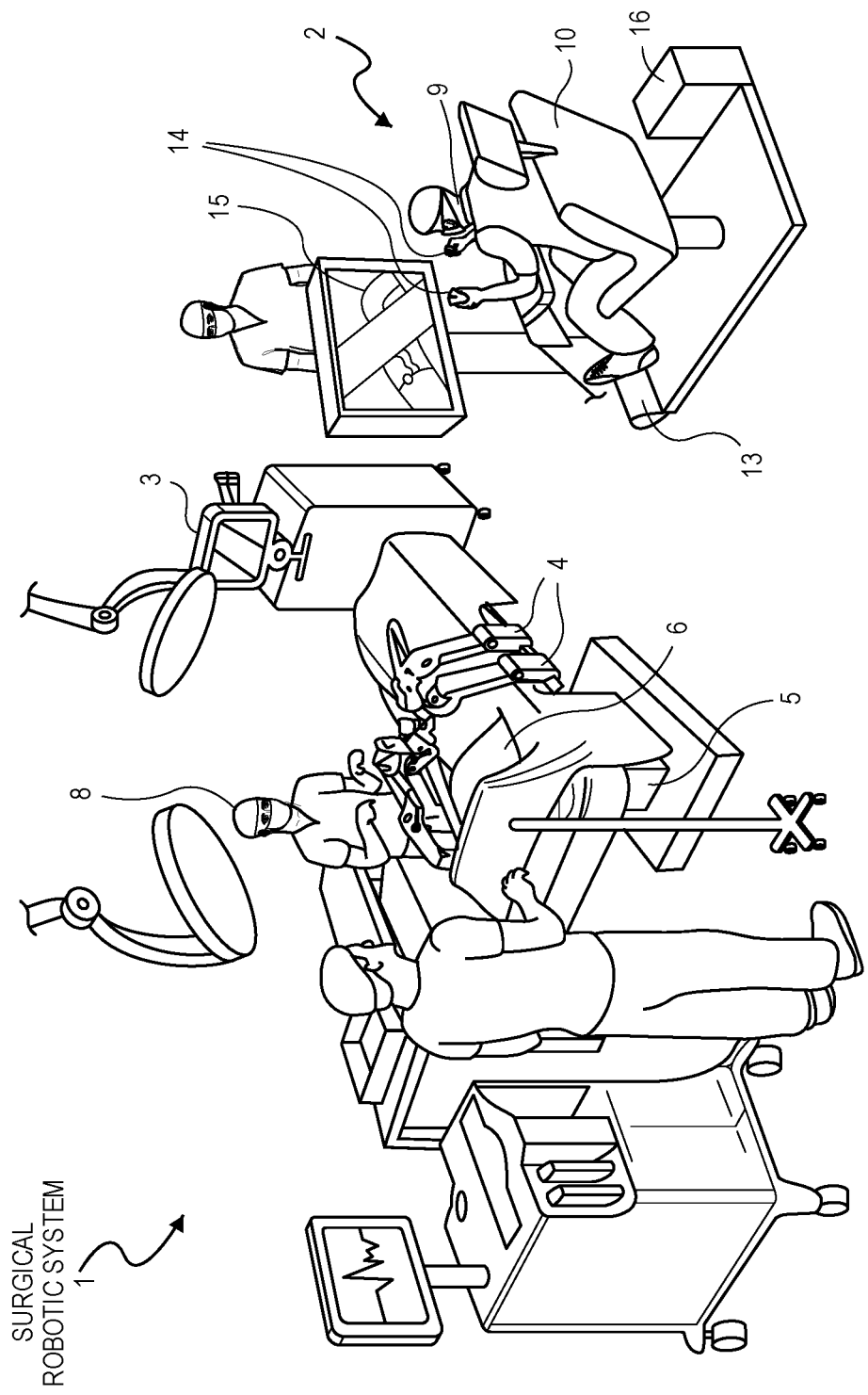
FIG. 1 is a pictorial view of an example surgical robotic system in an operating arena.

Referring to FIG. 1, this is a pictorial view of an example surgical robotic system 1 in an operating arena. The robotic surgical system 1 includes a user console 2, a control tower 3, and one or more surgical robotic arms 4 located at a surgical platform 5, e.g., a table, a bed, etc. The surgical robotic system 1 can incorporate any number of devices, tools, or accessories used to perform surgery on a patient 6. For example, the surgical robotic system 1 may include one or more surgical tools 7 used to perform surgery. A surgical tool 7 may be an end effector that is attached to a distal end of a surgical robotic arm 4, for executing a surgical procedure.

Each surgical tool 7 can be manipulated manually and/or robotically during the surgery. For example, the surgical tool 7 may be a tool used to enter, view, or manipulate an internal anatomy of the patient 6. In an embodiment, the surgical tool 6 is a grasper used to grasp tissue of the patient. The surgical tool 6 may be controlled manually, by a bedside operator 8; or it may be controlled robotically, by actuated movement of the surgical robotic arm 4 to which it is attached. The surgical robotic arms 4 are shown as a table-mounted system, but in other configurations the surgical robotic arms 4 may be mounted in a cart, ceiling or sidewall, or in another suitable structural support.

Generally, a remote operator 9, such as a surgeon or other operator, may use the user console 2 to remotely manipulate the surgical robotic arms 4 and/or the attached surgical tools 7, e.g., tele-operation. The user console 2 may be located in the same operating room as the rest of the surgical robotic system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the surgical robotic arms 4 and the surgical tools 7 (that are mounted on the distal ends of the surgical robotic arms.)

In some variations, the bedside operator 8 may also operate the surgical robotic system 1 in an "over the bed" mode, in which the beside operator 8 (user) is now at a side of the patient 6 and is simultaneously manipulating a robotically-driven tool (end effector as attached to the surgical robotic arm 4), e.g., with a handheld UID 14 held in one hand, and a manual laparoscopic tool. For example, the bedside operator's left hand may be manipulating the handheld UID to control a surgical robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the surgical robotic system 1 are in a stowed configuration or withdrawn configuration (to facilitate access to the surgical site.) Once access is completed, initial positioning or preparation of the surgical robotic system 1 including its surgical robotic arms 4 may be performed. Next, the surgery proceeds with the remote operator 9 at the user console 2 utilizing the foot-operated controls 13 and the UIDs 14 to manipulate the various end effectors and perhaps an imaging system to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the surgical robotic arms 4. Non-sterile personnel may also be present to assist the remote operator 9 at the user console 2. When the procedure or surgery is completed, the surgical robotic system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the surgical robotic system 1. The UID 14 may be communicatively coupled to the rest of the surgical robotic system 1, e.g., via a console computer system 16. The UID 14 can generate spatial state signals corresponding to the pose and movement of the UID 14, e.g. position and orientation of the handheld housing of the UID, and the spatial state signals may be input signals to control a motion of the robot arm actuator 17. The surgical robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment of the surgical robotic arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

Surgical robotic system 1 may include several UIDs 14, where respective control signals are generated for each UID that control the actuators and the surgical tool (end effector) of a respective surgical robotic arm 4. For example, the remote operator 9 may move a first UID 14 to control the motion of an actuator 17 that is in a left surgical robotic arm, where the actuator responds by moving linkages, gears, etc., in that surgical robotic arm 4. Similarly, movement of a second UID 14 by the remote operator 9 controls the motion of another actuator 17, which in turn moves other linkages, gears, etc., of the surgical robotic system 1. The surgical robotic system 1 may include a right surgical robotic arm 4 that is secured to the bed or table to the right side of the patient, and a left surgical robotic arm 4 that is at the left side of the patient. An actuator 17 may include one or more motors that are controlled so that they drive the rotation of a joint of the surgical robotic arm 4, to for example change, relative to the patient, an orientation of an endoscope or a grasper of the surgical tool 7 that is attached to that arm. Motion of several actuators 17 in the same surgical robotic arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the surgical platform 5 and the user console 2 may be through a control tower 3, which may translate user commands that are received from the user console 2 into robotic control commands that transmitted to the surgical robotic arms 4 on the surgical platform 5. The control tower 3 may also transmit status and feedback from the surgical platform 5 back to the user console 2. The communication connections between the surgical platform 5, the user console 2, and the control tower 3 may be via wired and/or wireless links, using any suitable ones of a variety of data communication protocols. Any wired connections may be optionally built into the floor and/or walls or ceiling of the operating room. The surgical robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

In one embodiment, a clutch freezes the surgical robotic arm(s) 4 and/or its attached surgical tool 7, so that one or a combination of those components does not respond to movements of an associated one or more UIDs 14. In some versions, the user, e.g. a surgeon, presses a clutch button or touches a sensing area (or alternatively, releases a clutch button or ceases to touch a sensing area) to disconnect the control input of the UID 14 from the surgical robotic system, and can reposition the UID 14 within the workspace without causing movement of any actuator. The clutch could be implemented as a mechanical device, a hardware electronic module, software executing on a processor, or combination of these. Sensing for user input to engage or disengage the clutch, operate or freeze the surgical robotic arm(s) 4 and/or surgical tool 7, could be made by a capacitive sensing or other clutch-tasked input device attached to or integrated with a UID 14. In some versions, if the user ceases to hold the UID 14, e.g., by setting the UID down, dropping the UID, etc., this is sensed by the clutch-tasked input device of the UID 14, and the system in response freezes one or more components, through the clutch, such as discussed above.

Fiber Bragg grating (FBG) sensors are optical fibers that are sensitive to strain, which can stem from mechanical and thermal stresses. The sensor is a piece of optical fiber with periodically placed refractive gratings in them. Fiber Bragg gratings may be achieved by inducing periodic changes in the refractive index of the fiber core that act like a mirror for a well determined wavelength called Bragg wavelength. The distance between the refractive gratings is correlated to the light transmitted or reflected inside the fiber core. Stretching or compressing the fiber changes this distance between the gratings, and therefore modulates the spectrum of light traveling inside the fiber. The wavelength of light that gets reflected from the refractive indices inside the fiber core is named "the Bragg wavelength". By monitoring the Bragg wavelength, the strain of the fiber can be predicted, and then turned into temperature, force or shape information depending on the application. FBG sensors are used for structural monitoring (attaching fibers on vehicle transport bridges and buildings to help predict the onset of critical events and structural failure/life), tracking of catheters and snake-like robotic manipulators (the shape of flexible medical instruments can be estimated while operating inside the human body and when no other means of visualization is feasible), temperature sensing (FBGs are integrated in ablation tools to measure temperature directly at the tip of the instrument in order to keep it at a desired level), and finally for force sensing (by attaching FBG sensors on medical instruments, tool-tissue interaction forces can be sensed at the tip of the instrument).

Figure 2:
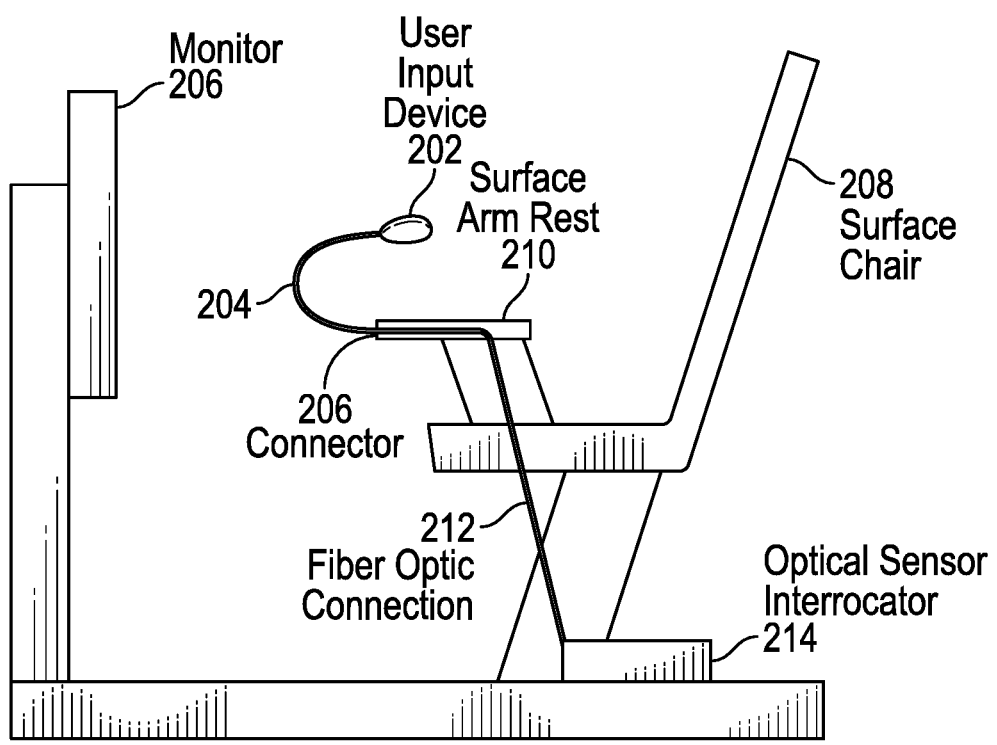
FIG. 2 depicts an example of a surgical robotic user input system or user console, with a handheld user input device whose pose is tracked using fiber Bragg grating sensors.

Various embodiments described herein include handheld user input devices that are controlled by the user for use in robotic surgery, i.e. surgical robotics, and a tracking system and method to determine the pose of these devices using fiber Bragg grating technology. In addition in some embodiments, there may be a means of determining the user applied pressure to the handheld user input devices. This system and method are used to enable a surgeon's input during teleoperation to perform remote control of surgical robotic instruments. For instance, FIG. 2 illustrates part of the user console 2—see FIG. 1—which is a component of a teleoperative robot-assisted surgical platform, and comprises one or more visualization devices (e.g. monitor 206), a surgeon chair 208, arm rests 210 on which the surgeon rests her arms during use of the robotic surgical system, a handheld user input device 202, connector 206 for coupling a fiber optic cable 204 to the arm rest 210 or the chair 208, an optional internal connection 212 between the fiber optic cable 204 and an optical sensing interrogator 214 (where the latter supports one or more input FBG sensor channels), and a processing unit (not shown in FIG. 2 but see FIG. 7). While only one input FBG sensor channel is shown, there may be more than one, e.g. one for a left hand UID and another for a right hand UID.

In the example surgical robotic user input system or user console of FIG. 2, a pose of the handheld user input device is tracked using fiber Bragg grating sensors. Fiber Bragg grating sensors are attached to and between the handheld user input device 202 and the arm rest 210, in the fiber optic cable 204. Generally, fiber Bragg grating sensors are considered intrinsic sensors, as they are part of the optical fiber inside of which a FBG is formed and do not require an electric power supply. The use of intrinsic sensors, without electrical wires and electrical or electronic components, makes some versions of the user input device 202 and fiber-optic cable 204 sterilizable, for example in an autoclave. In further embodiments, instead of or in addition to an FBG sensor, other types of optical fiber based intrinsic sensors could be used, such as Fabry-Perot interferometric sensors, and other types of interferometric sensors.

In this exemplary setup, the user (e.g. a surgeon) sits in a chair 208 and can view the monitor 206. The user's arms can be rested on the armrests 210, and the user holds one or more handheld user input devices 202 in each hand. One or more intrinsic fiber Bragg grating sensors are integrated into the fiber optic cable 204 that extends from the handheld user input device 202 to the arm rests 210. The fiber optic cable 204 is optically coupled to the optical sensing interrogator 214 which enables the FBG sensor data acquisition (see FIG. 3). Optionally, a fiber optic connection 212 enables the remote measurement of the FBG sensor data.

This setup allows the user to move the handheld user input device 202 freely to any position and in any orientation in space, while the system continuously computes the exact pose of the UID. The information flow during a sample operation is shown in FIG. 3.

Figure 3:
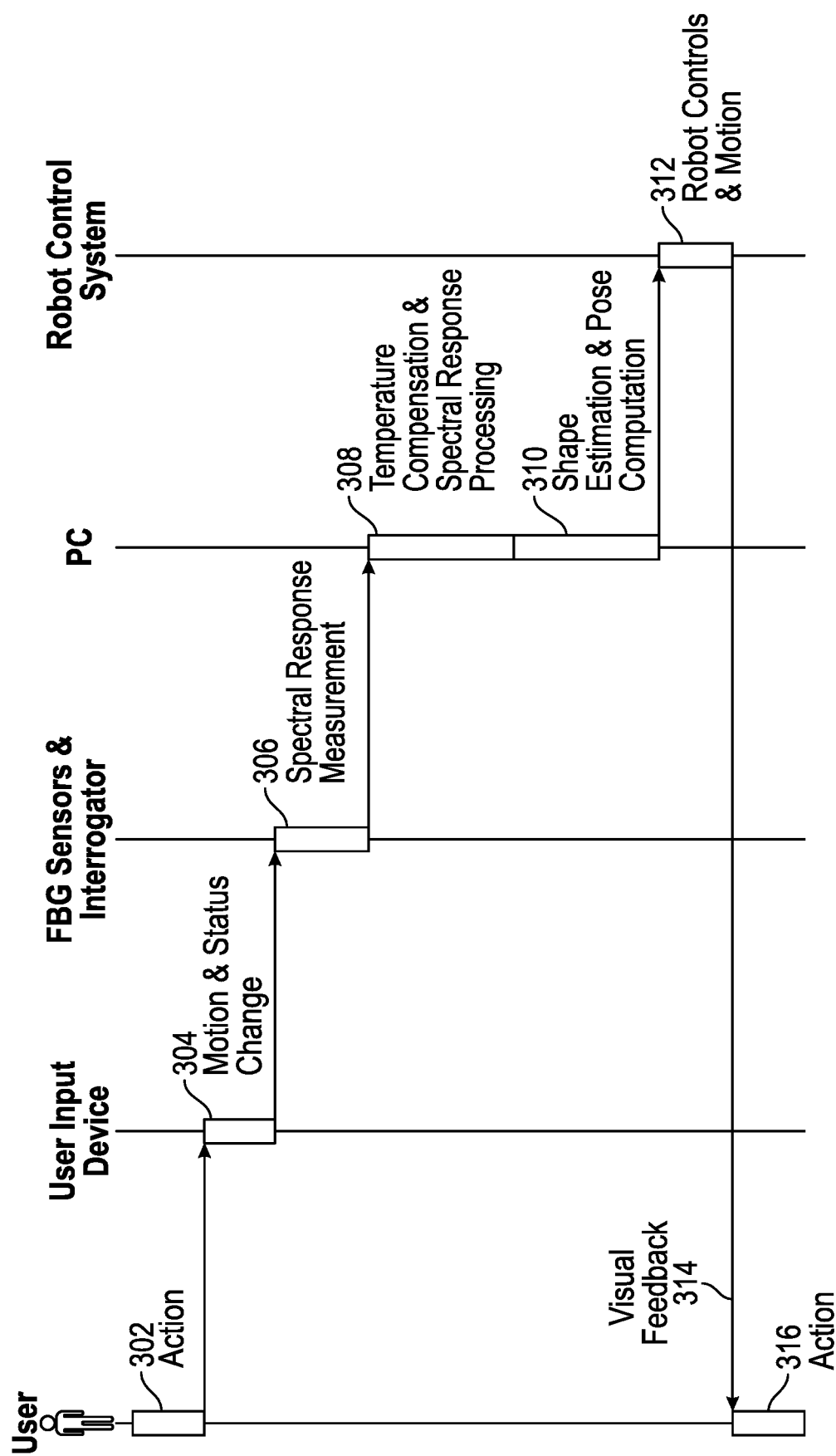
FIG. 3 is an information flow diagram for the surgical robotic user input system of FIG. 2.

FIG. 3 is an information flow diagram for the robotic surgical user input system of FIG. 2. User actions 302 cause position and status changes 304 on the handheld user input device 202, which influence the fiber Bragg grating sensors' spectral response. Based on the common and differential modes extracted from the spectral response 306, temperature compensated 308 shape and status estimates 310 are computed. The computed information can be used to control 312 a robotic device such as a surgical robotic arm and its attached tool for teleoperation, which is monitored by the user via visual feedback 314.

As the surgeon moves the handheld user input devices, the shape of the fiber(s) changes, influencing varying strain on the FBG sensors. In addition, there can be additional user inputs, such as squeezing (see FIG. 4) or push button, inducing strain onto other FBG fiber(s) within the handheld user input device. The applied strain on FBGs lead to changes in the fibers' spectral response, which is captured by the optical sensing interrogator. The shift in the Bragg wavelength of each sensor can be analyzed to obtain the common mode (e.g., average of sensor readings on each fiber core at the same position) and differential mode (deviation of each sensor output from the common mode) readings. The common mode can be used to predict ambient temperature changes, and cancel out undesired thermal drift in the sensors' response. The differential mode of sensors can be used to compute the shape of the connecting fiber, and therefore the position and orientation of the handheld user input device. The information from other FBG sensor(s) inside the handheld user input device can similarly define if the user has released or squeezing the handheld user input device. The computed information can then be used to generate motion commands for the robotic manipulator. In a further embodiment, the measurement of pressure or button click by the user's fingers can also be done by electronics, e.g., a printed circuit board (PCB), that is within the housing of the user input device 202 or that is electrically connected to the user input device 202, instead of or in addition to a FBG sensor.

Figure 4:
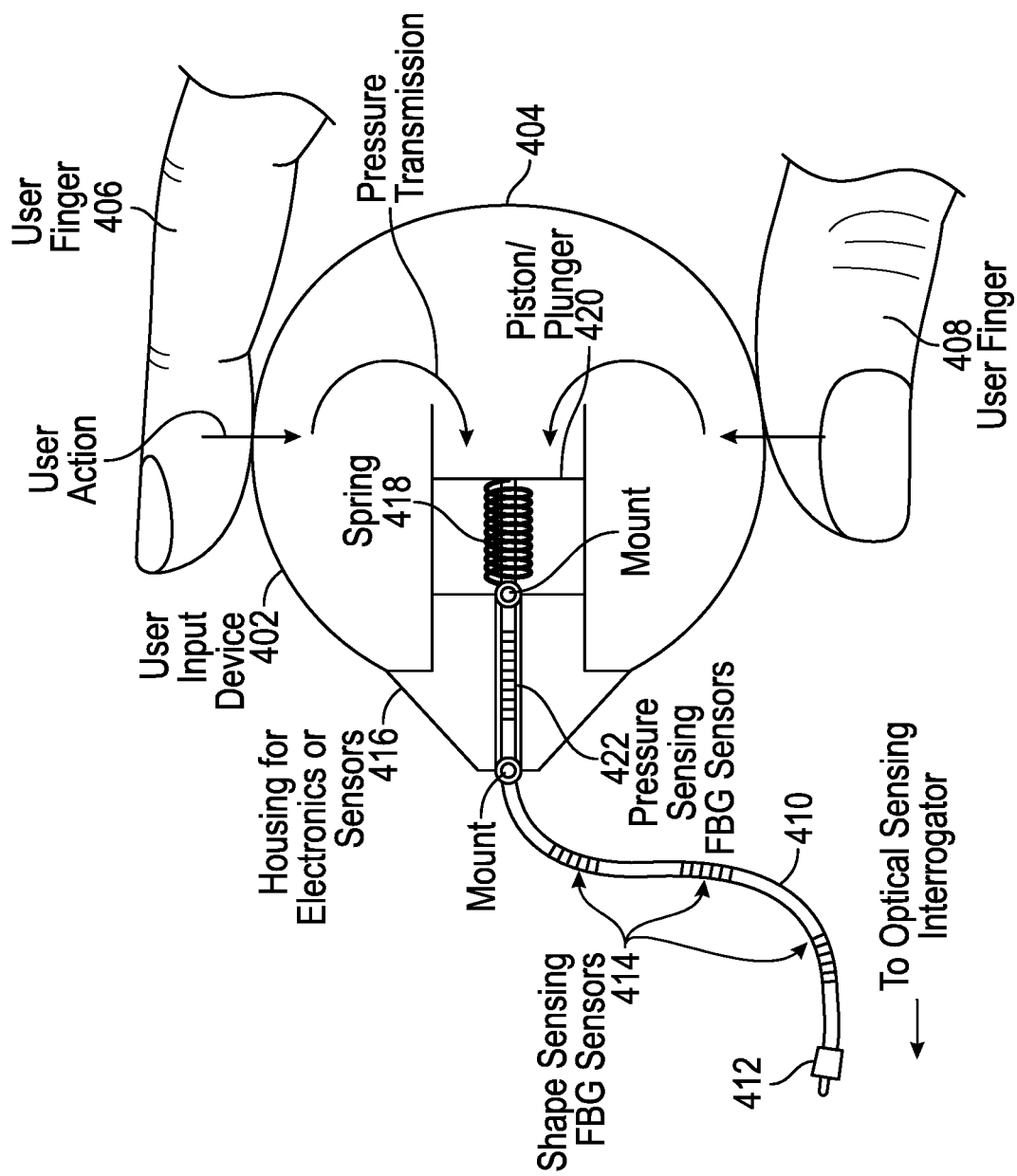
FIG. 4 depicts a sensing component for the surgical robotic user input system of FIG. 2.

To track the spatial and status information from the handheld user input devices, a sample architecture for integrating FBG sensors is shown in FIG. 4.

FIG. 4 depicts a sensing component for the robotic surgical user input system of FIG. 2. Shape sensing FBG sensors 414 are affixed in the fiber optic cable 410 between the frontal end of a handheld user input device 402 and the connector 412 site. The frontal end of the user input device 402 can function as a housing 416 for electronics or other sensors. Located inside the housing 416 is a pressure-sensitive FBG sensor 422, which is normally kept stretched by the spring loaded 418 piston 420. The rest of the handheld UID 402 is elastic, for example a squeeze bulb 404. By squeezing the elastic portion with fingers 406, 408, the user can apply variable pressure on the piston 420, which induces varying compression of the FBG sensor 422 inside the housing. In a further embodiment, pressure or a button click is sensed by a switch, touchpad, touchscreen or other touch-sensing electromechanical or electronic device attached to or integrated with the handheld UID 402, or induces a varying release of a pre-tensioned FBG sensor 422 inside the housing.

With reference to FIGS. 2-4, for tracking the position and orientation of the handheld user input device, fiber(s) are rigidly attached to the frontal end of the handheld user input device 202, 402 and connected to the optical sensing interrogator 214. As the user moves and rotates the handheld user input device 202, 402 in space, this connection will change its shape, which will be captured by the FBGs. The frontal end of the handheld user input device 202, 402 can be used to house other sensor(s). An example application is to use another FBG sensor 422 with a spring loaded 418 plunger 420 inside the proximal end of the handheld user input device 402. In this design, the proximal end can be an elastic enclosure held between the fingers 406, 408. By squeezing the elastic enclosure, the user can generate varying pressure, which will move the spring loaded 418 plunger 420 up and down, tensioning or compressing the FBG sensor 422. This enables capturing the status of the handheld user input device 402 precisely and quickly.

Figure 5:
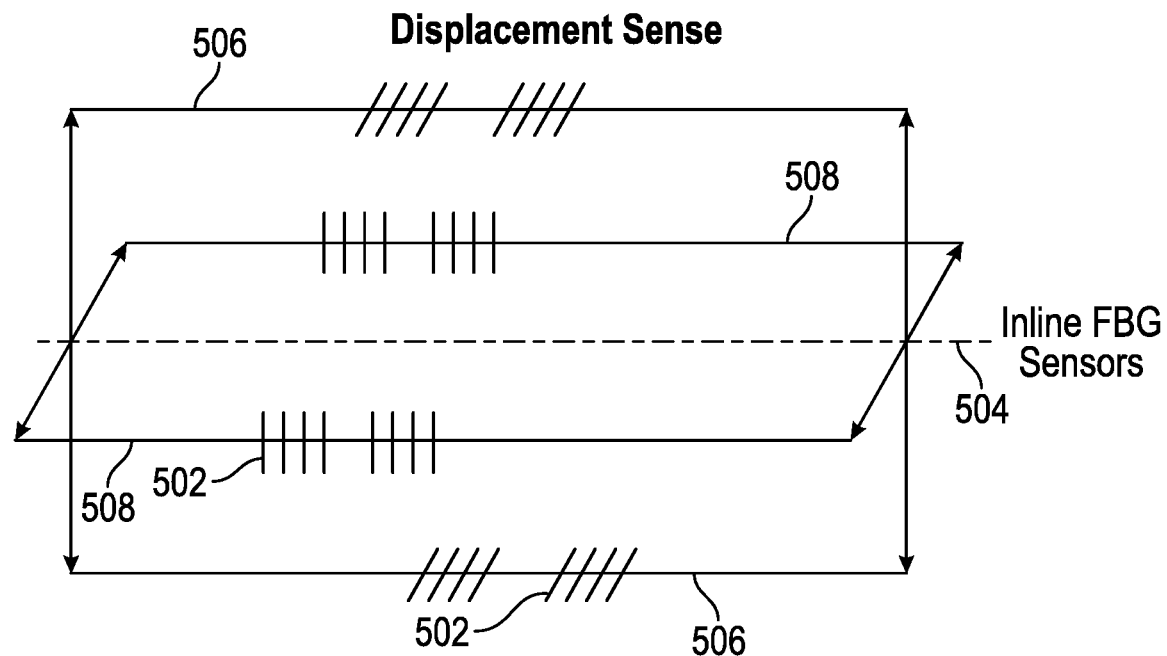
FIG. 5 depicts inline fiber Bragg grating sensors.

FIG. 5 depicts inline fiber Bragg grating sensors 502. Arranged inline relative to a longitudinal axis 504 of the fiber optic cable 204 connected to the handheld user input device 202 (see FIG. 2), these fiber Bragg grating sensors 502 respond to positional changes such as vertical or lateral displacement and bending of the fiber optic cable 204. Only a small number of the fiber Bragg sensors 502 are shown in the drawing, generally embodiments will have many more of these. Two optical fibers 506, with fiber Bragg sensors 502, are shown for detecting displacement in the vertical direction, through differential mode analysis, and two more optical fibers 508, with fiber Bragg sensors 502, are shown for detecting displacement in the lateral direction, also through differential mode analysis. Further embodiments could have more optical fibers with fiber Bragg sensors 502, for redundancy, accuracy improvement, or more directly sensing displacement in diagonal directions.

Figure 6:
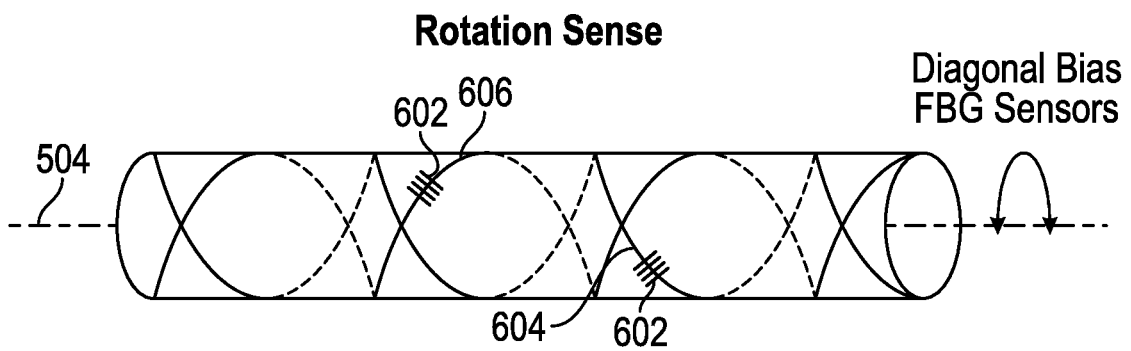
FIG. 6 depicts diagonal bias fiber Bragg grating sensors.

FIG. 6 depicts diagonal bias fiber Bragg grating sensors 602. Arranged at a nonzero, non-vertical angle, i.e., a diagonal bias, relative to the longitudinal axis 504 of the fiber optic cable 204 connected to the handheld user input device 202 (see FIG. 2), these fiber Bragg sensors 602 respond to rotational changes such as twisting of the fiber optic cable 204. Only a small number of the fiber Bragg sensors 602 are shown in the drawing, generally embodiments will have many more of these. One optical fiber 604 with fiber Bragg sensors 602 is shown spiraling around the fiber optic cable 204 as if a right-hand thread of a bolt or screw, and another optical fiber 606 with fiber Bragg sensors 602 is shown spiraling around the fiber optic cable 204 as if a left-hand thread. Rotation or twist of the fiber optic cable 204 in a given direction will generally compress fiber Bragg sensors 602 in one of the optical fibers and extend fiber Bragg sensors 602 in the other of the optical fibers, and vice versa for rotation in an opposing direction. Further embodiments could have more optical fibers with fiber Bragg sensors, for redundancy or accuracy improvement.

Figure 7:
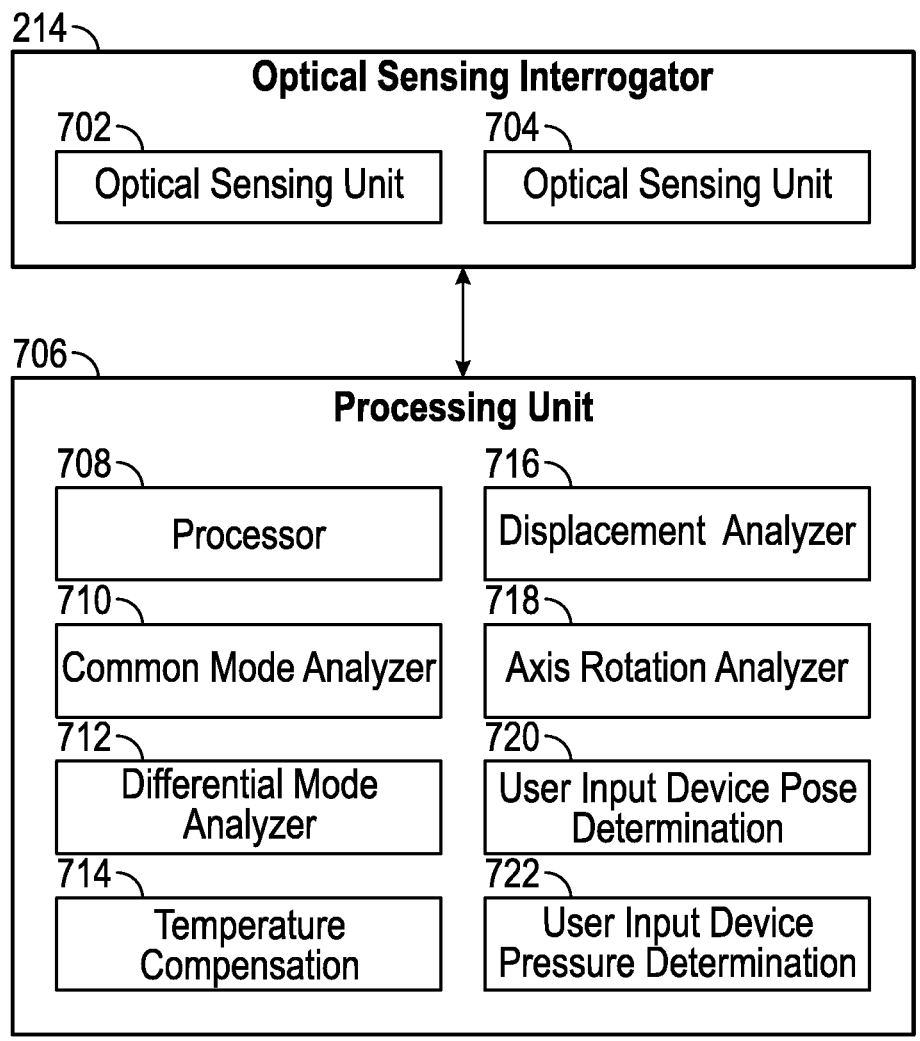
FIG. 7 is a block diagram of a processing unit and an optical sensing interrogator for use in the surgical robotic user input system of FIG. 2.

FIG. 7 is a block diagram of a processor-based optical sensing interrogator for use in the surgical robotic user input system of FIG. 2. The optical sensing interrogator 214 and processing unit 706 are shown as separate items, but could be integrated into a single unit in one embodiment. An optical sending unit 702 sends broad spectrum light out to the fiber optic cable 204 with the fiber Bragg grating sensors. Some of this light is spectrally modified and reflected back by the fiber Bragg grating sensors, and received by the optical sensing unit 704. In the processing unit 706, a processor 708 may be programmed by various software modules that are stored in memory, to perform analysis of the light received by the optical sensing unit 704. Note that at least some of the actions of the processor in executing these modules can alternatively be implemented in dedicated and separate hardware units. In some embodiments, the processing unit 706 is part of a computer system in the user console 2 or in the tower 3—see FIG. 1. A common mode analyzer 710 determines common mode modification of the light. A differential mode analyzer 712 determines differential mode modification of the light. A temperature compensation unit 714 determines temperature changes, and corrects for thermal drift in readings of the sensors, based on the common mode analysis. A displacement analyzer 716 determines three-dimensional displacement along the fiber optic cable, based on the differential mode analysis. An axis rotation analyzer 718 determines rotation along the fiber optic cable, such as rotation along the longitudinal axis of the fiber optic cable, or alternatively rotation relative to an axis of the user input device 202, 402 or another axis for another coordinate system, based on the differential mode analysis. A surgical robotic handheld user input device pose determination unit 720 determines Cartesian XYZ position and XYZ rotation, or pose, of the handheld user input device, based on the displacement analysis and axis rotation analysis. Alternatively, instead of Cartesian coordinates for the handheld user input device pose, polar coordinates or other coordinate systems could be used in variations. A handheld user input device pressure determination unit 722 determines pressure in the handheld user input device, based on the differential mode and/or common mode analysis, as appropriate to the arrangement of sensor(s) in the handheld user input device coupled to receive pressure.

Figure 8:
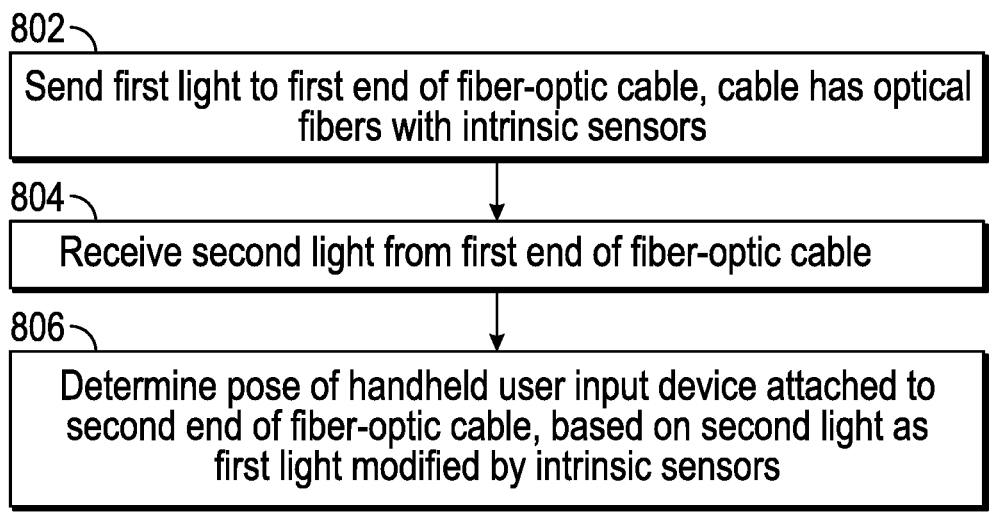
FIG. 8 is a flow diagram of a method of operating a surgical robotic user input system.

FIG. 8 is a flow diagram of a method of operating a surgical robotic user input system. The method is performed by a processor-based optical sensing interrogator with separate or integrated programmed processor as described with reference to FIG. 7, in one embodiment. In an action 802, first light is sent to a first end of a fiber optic cable. The fiber optic cable has optical fibers with intrinsic sensors. In some embodiments, the intrinsic sensors are fiber Bragg grating sensors.

In an action 804, second light is received from the first end of the fiber optic cable. In an action 806, a pose of a handheld user input device is determined. The handheld user input device is attached to the second end of the fiber optic cable. Determination of the pose is based on the second light, as the first light modified by the intrinsic sensors.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while FIG. 4 depicts a handheld user input device that transmits finger pressure to a spring-loaded piston compressing a fiber Bragg grating sensor, other arrangements for the handheld user input device are possible (e.g., levers, tension, a user input device without pressure sensing, other types of sensors, other arrangements of sensors, and various shapes for the handheld user input device). Where determining a shape of one of the intrinsic sensors is described, it should be appreciated that shapes of multiple intrinsic sensors can be determined. The description is thus to be regarded as illustrative instead of limiting.

What is claimed is:

1. A surgical robotic user input apparatus, comprising:
   a fiber optic cable having a plurality of intrinsic sensors therein, a first end with a connector and a second end;
   a handheld user input device (handheld UID) attached to the second end of the fiber optic cable, wherein the handheld UID comprises a squeeze bulb having therein a pressure coupling to a pressure sensing one of the plurality of intrinsic sensors; and
   the plurality of intrinsic sensors being configured to modify propagating light in the fiber optic cable to detect a pose of the handheld UID, the pose comprising a three-dimensional position of the handheld UID and a rotation of the handheld UID.

2. The surgical robotic user input apparatus of claim 1, further comprising:
   an optical sensing interrogator arranged to couple to the connector of the fiber optic cable.

3. The surgical robotic user input apparatus of claim 1, wherein the plurality of intrinsic sensors comprises a plurality of fiber Bragg grating sensors.

4. The surgical robotic user input apparatus of claim 1, wherein the plurality of intrinsic sensors comprises a plurality of interferometric sensors.

5. The surgical robotic user input apparatus of claim 1, wherein the fiber optic cable comprises:
   a first plurality of optical fibers having a first plurality of intrinsic sensors, arranged inline with respect to a longitudinal axis of the fiber optic cable; and
   a second plurality of optical fibers having a second plurality of intrinsic sensors, wrapped or woven at a bias with respect to the longitudinal axis of the fiber optic cable.

6. The surgical robotic user input apparatus of claim 1 wherein the fiber optic cable comprises a bundle of single-core optical fibers or a multi-core optical fiber, and wherein the plurality of intrinsic sensors are distributed discretely along a length of the single-core fibers or multi-core optical fiber.

7. The surgical robotic user input apparatus of claim 1, wherein the handheld UID comprises:
   the squeeze bulb having gas, liquid, gel or semisolid material therein;
   a diaphragm, piston or plunger within the squeeze bulb and exposed to the gas, liquid, gel or semisolid material; and
   a spring-loaded coupling from the diaphragm, piston or plunger to one or more of the plurality of intrinsic sensors, to compress or tension the one or more of the plurality of intrinsic sensors in response to finger or hand pressure on the squeeze bulb.

8. The surgical robotic user input apparatus of claim 1, wherein the handheld UID and fiber optic cable include no electrical devices and are sterilizable.

9. The surgical robotic user input apparatus of claim 1, further comprising:
   an optical sensing interrogator, arranged to couple to the fiber optic cable and transmit light to the plurality of intrinsic sensors, and to detect light returned from the plurality of intrinsic sensors; and
   a programmed processor to determine, based on the detected light, pressure exerted on the handheld UID, the pose of the handheld UID, and ambient temperature changes.

10. The surgical robotic user input apparatus of claim 1, further comprising:
    a touch-sensing device attached to or integrated with the handheld UID.

11. A method of operating a surgical robotic user input apparatus, the method comprising:
    sending first light into a fiber optic cable having a plurality of intrinsic sensors;
    receiving second light from the fiber optic cable, wherein the second light comprises the first light modified by the plurality of intrinsic sensors; and
    determining a pose, comprising a three-dimensional position and a rotation, of a handheld user input device (handheld UID) attached to the fiber optic cable, based on the detected second light, wherein determining the three-dimensional position of the handheld UID is based on differential mode analysis of the first light modified by a first subset of the plurality of intrinsic sensors, wherein the first subset is oriented inline with a longitudinal axis of the fiber optic cable.

12. The method of claim 11, further comprising:
    determining relative pressure or pressure change of the handheld UID, based on the second light received from the fiber optic cable.

13. The method of claim 11, further comprising:
    determining common mode modification of the first light, in the second light; and
    determining differential mode modification of the first light, in the second light.

14. The method of claim 11, further comprising:
    determining temperature change, based on detecting common mode modification of the first light, in the second light; and
    correcting for thermal drift in readings of the plurality of intrinsic sensors, based on the determined temperature change.

15. The method of claim 11, further comprising:
    determining a shape of one of the plurality of intrinsic sensors, based on detecting differential mode modification of the first light, in the second light, wherein the determining the pose is based on the determining the shape.

16. The method of claim 11, wherein the determining the pose comprises differential mode analysis of the second light as the first light modified by a plurality of fiber Bragg grating sensors that are a subset of the plurality of intrinsic sensors.

17. The method of claim 11, wherein the determining the pose comprises differential mode analysis of the second light as the first light modified by a plurality of interferometric sensors that are a subset of the plurality of intrinsic sensors.

18. The method of claim 11, wherein the determining the pose of the handheld UID comprises:
   determining the rotation of the handheld UID based on differential mode analysis of the first light modified by a second subset of the plurality of intrinsic sensors, wherein the second subset is oriented at a bias relative to the longitudinal axis of the fiber optic cable.

19. The method of claim 11, further comprising:
   determining a value of a compression or extension of one of the plurality of intrinsic sensors that is arranged to react to pressure of the handheld UID, through analysis of the first light modified by the intrinsic sensor.

20. The method of claim 11, further comprising:
   sending data regarding the pose of the handheld UID to a robotic controller in a surgical robotics system.

\* \* \* \* \*